United States Patent
Yershov

(10) Patent No.: US 7,463,353 B2
(45) Date of Patent: Dec. 9, 2008

(54) MODULAR, MICRO-SCALE, OPTICAL ARRAY AND BIODETECTION SYSTEM

(75) Inventor: Gennadiy M. Yershov, Willowbrook, IL (US)

(73) Assignee: UChicago Argonne, LLC, Chicago, IL (US)

( * ) Notice: Subject to any disclaimer, the term of this patent is extended or adjusted under 35 U.S.C. 154(b) by 316 days.

(21) Appl. No.: 11/444,241

(22) Filed: May 31, 2006

(65) Prior Publication Data

US 2007/0279631 A1 Dec. 6, 2007

(51) Int. Cl.
*G01J 3/30* (2006.01)
(52) U.S. Cl. ...................................................... 356/317
(58) Field of Classification Search ................. 356/317, 356/417; 250/458.1, 461.2; 436/172; 422/82.07–82.08
See application file for complete search history.

(56) References Cited

U.S. PATENT DOCUMENTS

| | | | |
|---|---|---|---|
| 5,962,329 A | 10/1999 | Ershov et al. | |
| 6,215,593 B1 * | 4/2001 | Bruce | 359/619 |
| 6,271,042 B1 | 8/2001 | Watson, Jr. et al. | |
| 6,329,661 B1 | 12/2001 | Perov et al. | |
| 6,407,395 B1 | 6/2002 | Perov et al. | |
| 6,458,584 B1 | 10/2002 | Mirzabekov et al. | |
| 6,620,623 B1 * | 9/2003 | Yershov et al. | 436/172 |
| 6,692,972 B1 | 2/2004 | Yershove et al. | |
| 6,995,901 B2 | 2/2006 | Heffelfinger | |
| 7,189,367 B2 * | 3/2007 | Yamamoto et al. | 422/100 |
| 2007/0217963 A1 * | 9/2007 | Elizarov et al. | 422/130 |

* cited by examiner

*Primary Examiner*—Kara E Geisel
*Assistant Examiner*—Abdullahi Nur
(74) *Attorney, Agent, or Firm*—Joan Pennington

(57) ABSTRACT

A modular, micro-scale, optical array and biodetection device for quantifying fluorescence intensities of a plurality of substantially separated, and dimensionally uniform elements of a bioarray that are located at known positions on a plain support includes a light guide that directs bioarray illumination light from a respective light source to opposing sides of the plain support. An optical module collecting light individually from the bioarray elements includes an optical member, a filter, and a sensor, such as a CCD chip. The optical member collects and transfers emitted light from the bioarray elements via the filter to the sensor. The filter transfers light from the elements having a predefined wavelength spectrum and blocks light outside the predefined wavelength spectrum. The sensor receives transferred light from the elements and produces a signal corresponding to respective elements of the bioarray.

14 Claims, 3 Drawing Sheets

MODULAR, MICRO-SCALE, OPTICAL ARRAY AND BIODETECTION SYSTEM

The United States Government has rights in this invention pursuant to Contract No. W-31-109-ENG-38 between the United States Government and Argonne National Laboratory.

FIELD OF THE INVENTION

The present invention relates to advanced micro-scale biosensors for use in defense, healthcare and biosecurity situations, and more particularly to an integrated modular optical system based on micro-lens array technology that is consistent in scale and dimensionality with the most common biochip form factors, and a reaction chamber and temperature control subsystem that unifies the optical and biochip components into a hand-held, low cost, integrated device for biological and chemical sensing, diagnostics and field deployment.

DESCRIPTION OF THE RELATED ART

Biochips after being incubated, for example, with a sample solution containing fluorescent labeled target molecules typically are assayed using either a microscope equipped with a charge coupled device (CCD) camera or a laser scanner. To acquire large volume of digital data (1-100 MB per image) in a reasonable time these devices employ sophisticated optical, mechanical, and electronic components, which results in high cost of the hardware used. Regardless of the technique of fluorescence measurement used, all known biochip analyzers are high-resolution imaging instruments. For example, this means that their output data is essentially a digital image of the chip composed of approximately 1000N elementary data points, where N represents the number of biochip immobilization sites.

As a biochip user is typically interested in relative fluorescence intensities of the immobilization sites, an image as the output data format is highly redundant and requires further processing before the data can be analyzed. This may include signal integration over the immobilization sites, background subtraction, and normalization. The image processing is especially difficult in the case of analyzers based on widefield microscopes, in which both the sensitivity and the image background are inherently non-uniform. With increasing complexity of biochips, the software for processing the fluorescence data becomes increasing intricate and rather demanding in terms of computer memory and processor speed.

U.S. Pat. No. 6,329,661 issued Dec. 11, 2001 to Alexander Perov et al. and assigned to the present assignee discloses a laser biochip scanner device used to detect and acquire fluorescence signal data from biological microchips or biochips and a technique of reading biochips referred to as Discrete Scanning (or Row Scanning). In contrast to the imaging scanners, this device scans exclusively the rows of a biochip array, the beam focal spot being adjusted to match the size of the array elements. The scanner employs a HeNe laser emitting at 594 nm to excite Texas Red-labeled target molecules, an optical system with a fiber-optic output for delivery of the excitation light to a miniature scanning head, and a low-noise photodiode as a fluorescence detector. A computer-controlled positioning system is used to move the scanning head in both X and Y directions to monitor the intensity of fluorescence for each element of a 2D biochip array. This setup provides a detection threshold and dynamic range close to those of commercially available biochip readers. In the same time, it is much less demanding in terms of the amplifiers bandwidth, analog-to-digital conversion rate, optical resolution, and scanning mechanics parameters.

U.S. Pat. No. 6,407,395 issued Jun. 18, 2002 to Alexander Perov et al. and assigned to the present assignee discloses a portable biochip scanner device used to detect and acquire fluorescence signal data from biological microchips (biochips). The portable biochip scanner device employs a laser for emitting an excitation beam. An optical fiber delivers the laser beam to a portable biochip scanner. A lens collimates the laser beam, the collimated laser beam is deflected by a dichroic mirror and focused by an objective lens onto a biochip. The fluorescence light from the biochip is collected and collimated by the objective lens. The fluorescence light is delivered to a photomultiplier tube (PMT) via an emission filter and a focusing lens. The focusing lens focuses the fluorescence light into a pinhole. A signal output of the PMT is processed and displayed.

U.S. Pat. No. 6,620,623 issued Sep. 16, 2003 to Gennadiy M. Yershov et al. and assigned to the present assignee discloses a method of illumination and illumination apparatus in a biochip reader. Illumination is provided by a non-collimated laser source or a light emitting diode (LED). The light is directed to opposing sides of a glass substrate by a pair of optical fiber bundles. The glass substrate carries a bioarray. Each of the optical fiber bundles are splayed out to make a fan, the fan being one fiber thick and defining a line of optical fiber faces. This process randomizes any non-uniformity in the illumination source, creating a more uniform illumination source. A respective divergent diffuser engages each row of optical fiber faces coupling and diffusing light substantially evenly through the opposing sides of the glass substrate to illuminate the bioarray supported by the glass substrate. The glass substrate functions as a secondary light guide. The divergent diffusers separate the optical fiber faces from the edges of the glass substrate, protecting the optical fibers from mechanical damage. A glass holder supports the glass substrate carrying the bioarray. The glass holder including a plastics springs member in spring contact engagement with the glass substrate for positioning said bioarray in a focal plane. Light also can be directed to opposing ends of the glass substrate by a second pair of optical fiber bundles. Also a single optical fiber bundle can be used to direct light in one side of the glass substrate or three optical fiber bundles can be used to direct light into the glass substrate. This method of illumination provides a superior signal to noise ratio as compared with conventional illumination systems.

U.S. Pat. No. 5,962,329 issued Oct. 5, 1999 to Gennady M. Ershov et al. and assigned to the present assignee discloses a method and a device for dispensing microdoses of aqueous solutions, whereby the substance is transferred by the free surface end of a rodlike transferring element; the temperature of the transferring element is maintained at essentially the dew point of the ambient air during the transfer. The device may comprise a plate-like base to which are affixed a plurality of rods; the unfixed butt ends of the rods are coplanar. The device further comprises a means for maintaining the temperature of the unfixed butt ends of the rods essentially equal to the dew point of the ambient air during transfer of the aqueous substance.

U.S. Pat. No. 6,458,584 issued Oct. 1, 2002 to Andrel Mirzabekov et al. and assigned to the present assignee discloses using customized oligonucleotide microchips as biosensors for the detection and identification of nucleic acids specific for different genes, organisms and/or individuals in the environment, in food and in biological samples. The microchips are designed to convert multiple bits of genetic information into simpler patterns of signals that are interpreted as a unit. Because of an improved method of hybridizing oligonucleotides from samples to microchips, microchips are reusable and transportable. For field study, portable laser or bar code scanners are suitable.

U.S. Pat. No. 6,692,972 issued Feb. 17, 2004 to Gennadiy M. Yershov et al. and assigned to the present assignee discloses a device for producing microscopic arrays of molecules. The device comprises a plurality of inverted cavities containing solutions, a substrate adapted to be received by the cavities for extracting the solutions, a substrate for depositing the extracted solutions onto a location on a matrix; and a quality control monitoring system for verifying that the solutions are deposited onto the location on the matrix. A process for producing an array of molecules also is provided, the process comprising providing a plurality of inverted solution cavities, wherein each cavity contains a solution; extracting each solution from its respective inverted cavity; loading each solution at a predetermined position in an array; and verifying that each solution is loaded onto its respective position in the array.

There is a need for an inexpensive, hand-held, multi-purpose field device for users with little training to detect the presence of molecular targets, biological and chemical, in complex samples such as water, dirt, air, and food.

Microarray and related "chip-based" sensing technologies have demonstrated their power and utility as multiple sensors in laboratory settings for the analysis of peptides, proteins, carbohydrates, enzymes, nucleic acids, nerve agents, and other small molecules that cover a large number of the targets of interest for national defense and public health agencies. Whereas the biological recognition elements and chip-scale sensing elements have already been developed at the micro- and nano-scale, the supporting hardware and analysis equipment continues to be relatively large, power intensive, and expensive due to current optical designs in CCD cameras and lenses, scanning imagers, and limitations in commercially available light sources. This lag in development of miniaturized electro-optical detection around biochip sensors must be addressed in order to meet the national security goal of biological and chemical sensors which are readily portable, accurate and easy for the relatively un-skilled person to use.

Principal aspects of the present invention are to provide a modular, micro-scale, optical array and biodetection device including an integrated modular optical system and optionally including a reaction chamber and temperature control subsystem that unifies the optical and biochip components into a hand-held, low cost, integrated device for biological and chemical sensing, diagnostics and field deployment.

Other important aspects of the present invention are to provide such a modular, micro-scale, optical array and biodetection device substantially without negative effect and that overcome some of the disadvantages of prior art arrangements.

SUMMARY OF THE INVENTION

In brief, a modular, micro-scale, optical array and biodetection device is provided for quantifying fluorescence intensities of a plurality of substantially separated, and dimensionally uniform elements of a bioarray that are located at known positions on a plain support. A light guide directs bioarray illumination light from a respective light source to opposing sides of the plain support. An optical module collecting light individually from the bioarray elements includes an optical member, a filter, and a sensor. The optical member collects and transfers emitted light from the bioarray elements via the filter to the sensor. The filter transfers light from the elements having a predefined wavelength spectrum and blocks light outside the predefined wavelength spectrum. The sensor receives transferred light from the elements and produces a signal corresponding to respective elements of the bioarray.

In accordance with features of the invention, the sensor is a charge-coupled-device (CCD) chip. The optical member includes at least one of a micro-lens array and a fiber optic faceplate. The micro-lens array focuses emitted light from the bioarray elements having consistent scale and dimensionality with the bioarray elements. The fiber optic faceplate has consistent scale and dimensionality with the bioarray elements transferring emitted light from the bioarray elements substantially without change.

In accordance with features of the invention, a modular reaction chamber includes at least two ports. A temperature control stage is coupled to the reaction chamber for controlling temperature in a range between from +4° C. and +95° C. A plurality of the optical modules each collecting light individually from the bioarray elements of an associated bioarray provides a plurality of consecutive biodetection stages. A plurality of the consecutive biodetection stages is arranged in parallel providing concurrent, consecutive biodetection stages.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1A:
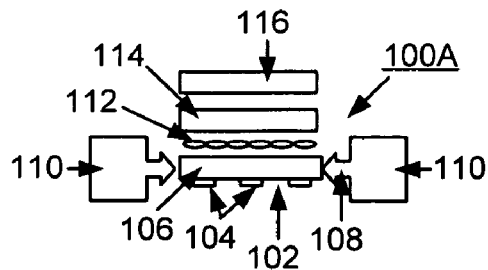
FIGS. 1A-1H are schematic and block diagram representations each illustrating a respective micro optical module for implementing biodetection methods in accordance with the preferred embodiment.

In accordance with features of the invention, an integrated modular optical system based on micro-lens array technology is provided that is consistent in scale and dimensionality with the most common biochip form factors, and a reaction chamber and temperature control subsystem are provided that unify the optical and biochip components into a hand-held, low cost, integrated device for biological and chemical sensing, diagnostics and field deployment. A new modular optical system is provided that collects light individually from each biosensor element at the micro scale. A modular, micro-scale, optical array and biodetection device is provided for quantifying fluorescence intensities of a plurality of substantially separated, and dimensionally uniform elements of bioarray that are located at known positions on a plain support. The modular, micro-scale, optical array and biodetection device of the invention can detect the absorption of light depending on a particular analysis being made.

Having reference now to the drawings, FIGS. 1A-1H illustrate a respective micro-optical module 100A-100H for implementing biodetection methods in accordance with the preferred embodiment. In FIGS. 1A-1H, the same reference characters are used for identical or similar devices. The micro-optical modules 100A-100H allow optimizing a biodetection system with respect to requirements for a particular application and a particular bioarray platform being used.

Each of the micro-optical modules 100A-100H is coupled to an associated bioarray 102 to provide a respective modular, micro-scale, optical array and biodetection device or system for quantifying fluorescence intensities of a plurality of substantially separated, and dimensionally uniform elements 104 of the bioarray that are located at known positions on a plain support 106, such as a glass or plastic slide. A light guide 108 directs bioarray illumination light from a respective light source 110 to opposing sides of the plain support 106. Optionally a mask member (not shown) is positioned between the respective micro-optical modules 100A-100H and the associated bioarray 102 corresponding to the bioarray elements 104 to limit light from inter-space between elements 104 of the bioarray of the respective micro-optical modules.

Light guides 108 and light sources 110 advantageously are implemented as disclosed in the above identified U.S. Pat. No. 6,620,623. The subject matter of U.S. Pat. No. 6,620,623 is incorporated herein by reference.

In the micro-optical modules 100A-100F and 100G in FIGS. 1A-1F, and 1H, the elements 104 of each respective associated bioarray 102 are located at a lower surface of the plain support 106. In FIG. 1G, the associated bioarray 102 is oriented with the elements 104 located at an upper surface of the plain support 106.

Illumination is provided, for example, light source 110 implemented by a low power (3-5 mW) non-collimated laser diode assembled with fiber optic light guide 108 emitting at specific wavelength such as, between 470 nm and 650 nm. Alternatively, a light emitting diode (LED) coupled with optical filter can also be used as the illumination source 110. The optical filter coupled to the LED light source 110 includes various standard filters, for example: bandpass filters, longpass or shortpass barrier filters, and rejection band filters. For example, an LED to implement the LED light source 110 is commercially available from the Newark catalog that provides intensity equivalent to 5-10 mW, Super bright LED, green, 150 mcd, 50 deg, at www.newark.com. An explanation how to translate mili-candela units to miliwatts can be found in the Basic Radiometry manual, http://www.opsci.com/technical.

Each optical module 100A-100H collecting light individually from the bioarray elements 104 includes at least one optical member 112, a filter 114, and a sensor 116. The optical member 110 collects and transfers emitted light from the bioarray elements 104 via the filter 114 to the sensor 116. The filter 114 transfers light from the elements having a predefined wavelength spectrum and blocks light outside the predefined wavelength spectrum. The sensor 116 receives transferred light from the elements and produces a signal corresponding to respective elements 104 of the associated bioarray 102.

The elements 104 of the bioarray or biochip 102 include, for example, a plurality of biochip gel pads 104 each containing specific probes. Light illuminate bioarray from inside the support 106 and labeled targets from a sample matching to the probes emit fluorescence of the specific wavelength under the illumination. Resulting light is gathered, filtered and transferred to the sensor 116, such as a CCD chip, of the respective modules 100A-100H. Filter 114 blocks or cutoffs some light and transfers only light of specific wavelength from the label or labels of the targets. Resulting light projected onto CCD chip sensor 116 from individual elements 104 of bioarray 102 do not overlap with projections of light from other elements 104 so that defocusing does not effect the quality of detection, as shown in the Tables 1 and 2 below.

Various filters can be used to implement the filter 114, for example, multiple filters of BrightLine sets optimized for fluorescence microscopy from Semrock of Rochester, N.Y. 14624 at www.semrock.com. CCD chip sensor 116 can be implemented with Full Frame CCD Image Sensor CCD486 from Fairchild Imaging of Milpitas, Calif. 95035 at www-.fairchildimaging.com.

A single micro-lens array or a fiber optic faceplate or a combination of one or more micro-lens arrays and fiber optic faceplates selectively defines the optical member 110 for collecting and transferring emitted light from the bioarray elements 104. The optical member micro-lens array 110 focuses emitted light from the bioarray elements having consistent scale and dimensionality with the bioarray elements 104. The optical member fiber optic faceplate 110 has consistent scale and dimensionality with the bioarray elements 104 transferring emitted light from the bioarray elements substantially without change.

Referring now to FIG. 1A, in optical module 100A the optical member 110 is defined by a micro-lens array positioned between the filter 114 and the bioarray 102. The optical member micro-lens array 110 focuses emitted light from the bioarray elements 104 of the bioarray 102.

The optical member micro-lens array 110 also is commercially available from New Jersey Nanotechnology Consortium of Murray Hill, N.J. 07974 at www.njnano.org. The optical member micro-lens array 110 also is commercially available from MEMS Optical, Inc. of Huntsville, Ala. 35806 at www.memsoptical.com.

Figure 1B:
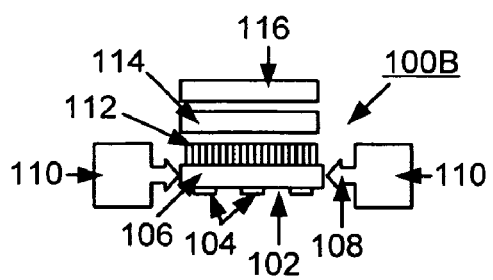

Referring now to FIG. 1B, in optical module 100B the optical member 110 is defined by a fiber optic faceplate positioned between the filter 114 and the bioarray 102. The optical member fiber optic faceplate 110 transfers emitted light from the bioarray elements 104 of the bioarray 102. The optical member fiber optic faceplate 110 typically includes optical fibers having a diameter in a range of 3-6 microns.

The optical member fiber optic faceplate 110 is the optical equivalent of a zero thickness window providing a high dielectric strength vacuum interface that can also be used for field-flattening, distortion correction and contrast enhancement. Faceplates 110 are commercially available in round, and square shapes from Incom Inc. of Charlton, Mass. 01507 at www.incomusa.com.

Figure 1C:
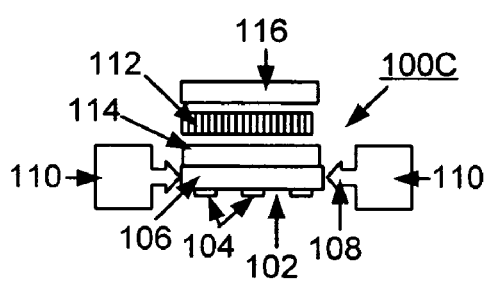

Referring now to FIG. 1C, in optical module 100C, the optical member 110 is defined by a fiber optic faceplate positioned between the filter 114 and the sensor 116. The optical member fiber optic faceplate 110 transfers the filtered light to the sensor 116.

Figure 1D:
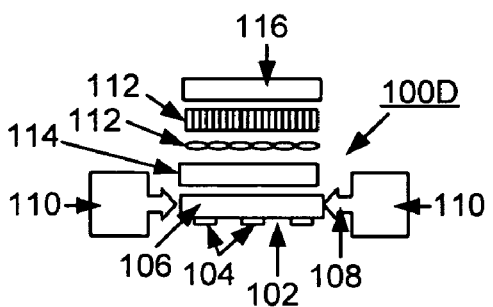

Referring now to FIG. 1D, in optical module 100D, the optical member 110 includes a combination of a fiber optic faceplate and a micro-lens array positioned between the filter 114 and the sensor 116. The combination of the optical member fiber optic faceplate 110 and the optical member micro-lens array 110 transfers the filtered light to the sensor 116.

Figure 1E:
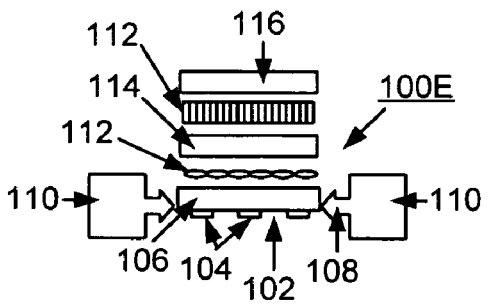

Referring now to FIG. 1E, in optical module 100E, the optical member 110 also includes a combination of a fiber optic faceplate and a micro-lens array. The filter 114 is positioned between the optical member fiber optic faceplate 110 and the optical member micro-lens array 110 with the optical member fiber optic faceplate 110 located proximate the sensor 116.

Figure 1F:
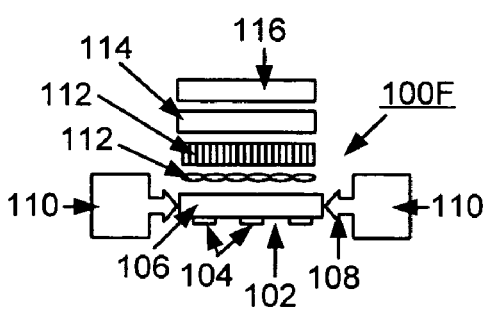
Figure 1G:
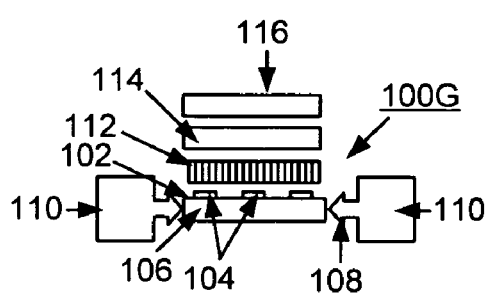

Referring now to FIG. 1F, in optical module 100F, the optical member 110 also includes a combination of a fiber optic faceplate and a micro-lens array. In optical module 100F, the filter 114 is positioned proximate the sensor 116 above the optical member fiber optic faceplate 110 and the optical member micro-lens array 110 with the optical member micro-lens array positioned proximate the bioarray 102.

Referring now to FIG. 1G, in optical module 100B the optical member 110 is defined by a fiber optic faceplate positioned below the filter 114 proximate to the bioarray elements 104 of the bioarray 102 that are located on the upward surface of plain support 106.

Figure 1H:
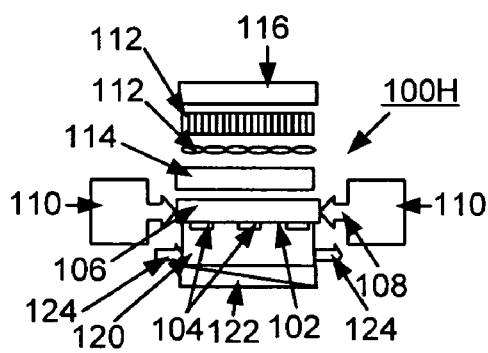

Referring now to FIG. 1H, in optical module 100H, the optical member 110 includes a combination of a fiber optic faceplate and a micro-lens array positioned between the filter 114 and the sensor 116 located between the sensor 116 and the bioarray 102. A reaction chamber 120 and a temperature stage 122 provide thermo-melt discrimination of abnormal stable mismathces. The reaction chamber 120 includes at least two ports 124 and contains the bioarray elements 104 of the bioarray 102. The temperature control stage 122 is coupled to the reaction chamber 120 for controlling temperature in a range between from +4° C and +95° C.

The temperature control stages 122 advantageously are implemented as disclosed in the above identified U.S. Pat. Nos. 5,962,329 and 6,692,972. The bioarray 102 advantageously are implemented in accordance with methods disclosed in the above identified U.S. Pat. Nos. 5,962,329; 6,692, 972; and 6,458,584. The subject matter of U.S. Pat. Nos. 5,962,329; 6,692,972; and 6,458,584 is incorporated herein by reference.

Figure 2:
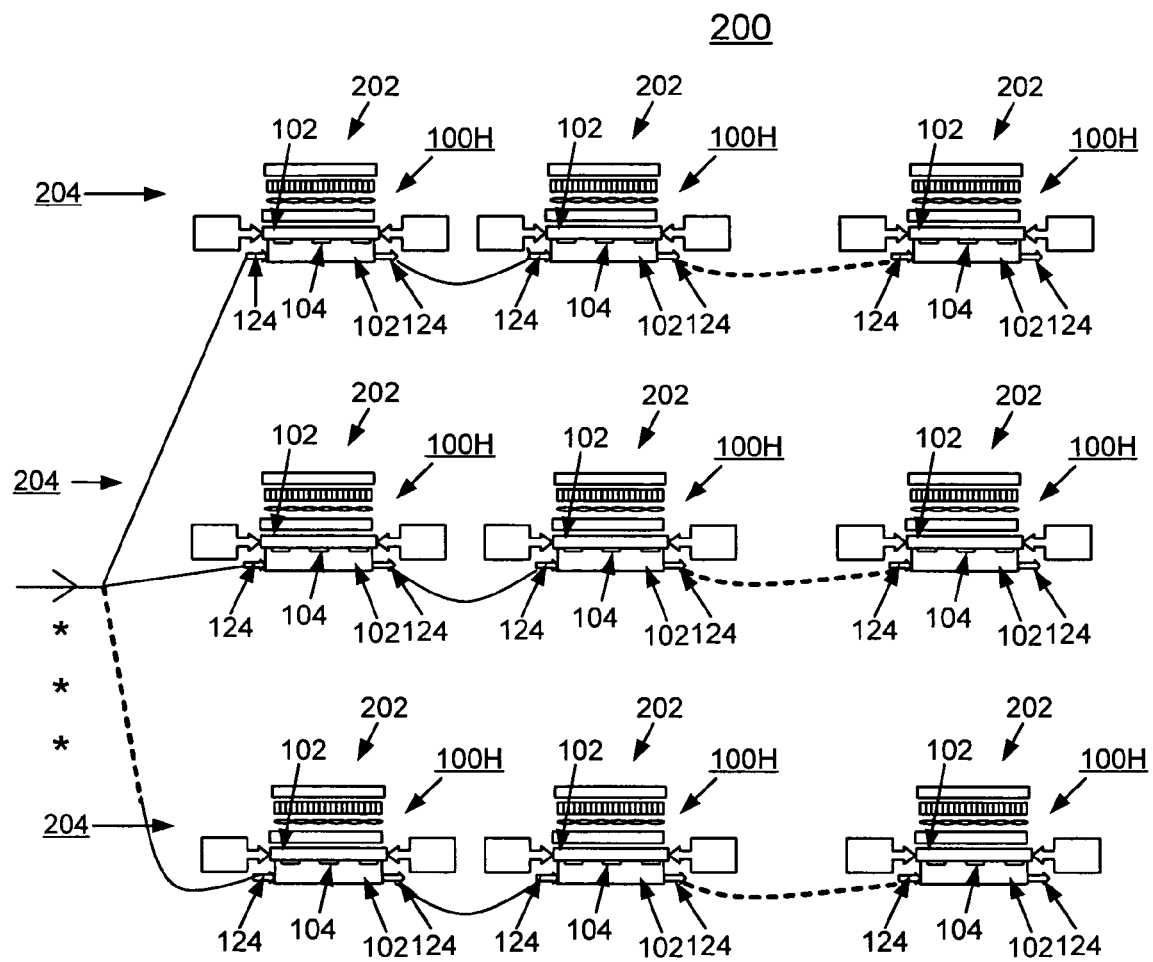
FIG. 2 is a schematic diagram representation illustrating a plurality of micro optical modules for implementing biodetection methods in accordance with the preferred embodiment.

Referring now to FIG. 2, there is shown biodetection system generally designated by the reference character 200 in accordance with the invention. Biodetection system includes a plurality of consecutive biodetection stages 202. A plurality of rows 204 of the consecutive biodetection stages 202 also enables concurrent, consecutive biodetection stages.

Each of the biodetection stages 202 includes a respective optical module 100H collecting light individually from the bioarray elements 104 of a bioarray 102 contained within an associated reaction chamber 120 that is optionally coupled to an associated temperature control stage 122.

Figure 3:
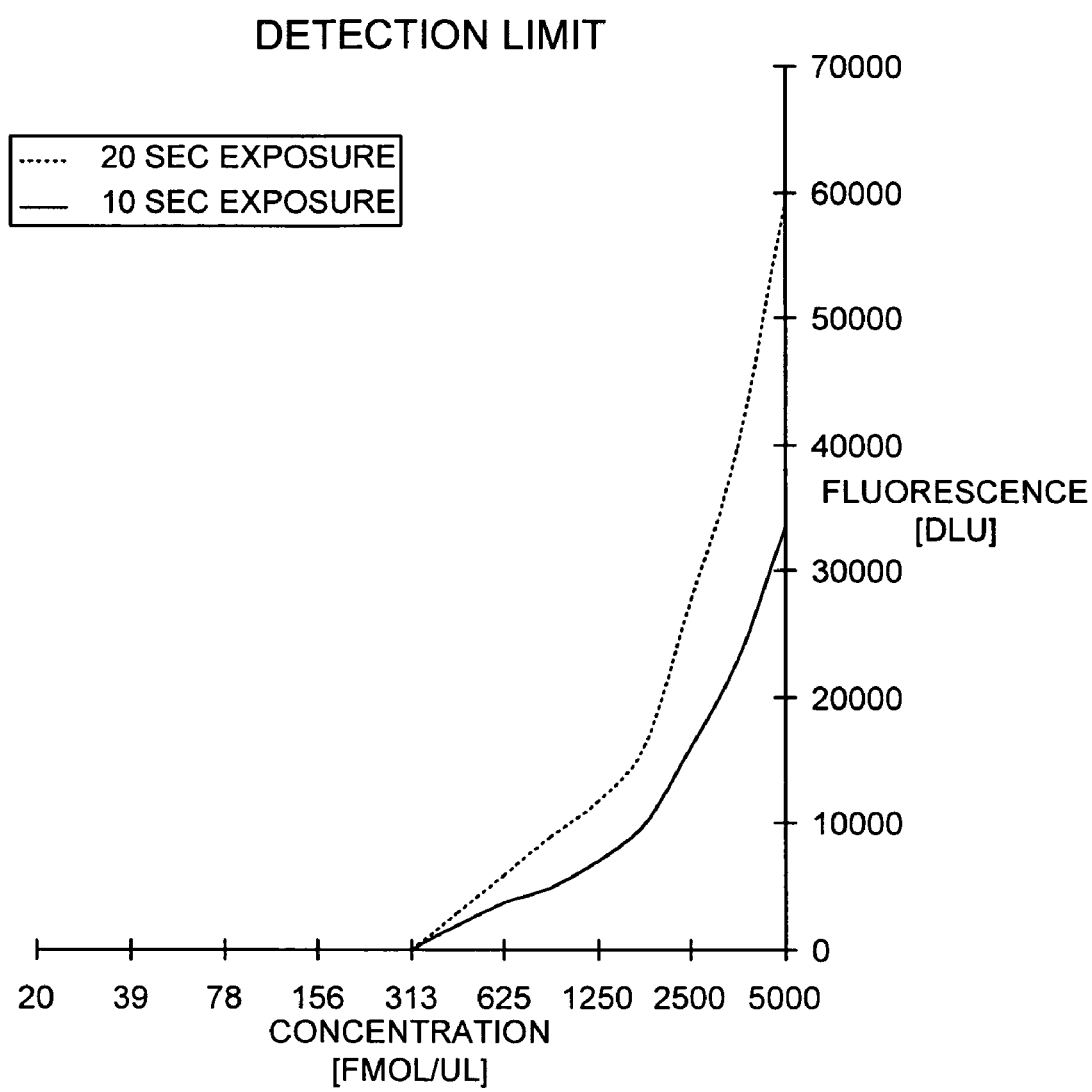
FIG. 3 is a chart illustrating measured and averaged fluorescence intensities in digital luminance units (DLUs) shown relative the vertical axis and concentration in fmol/ul shown relative the horizontal axis detection limit for 10 and 20 second exposures in accordance with the preferred embodiment.

Referring now to FIG. 3, measured and averaged fluorescence intensities in digital luminance units (DLUs) shown relative the vertical axis and concentration in fmol/ul shown relative the horizontal axis using a bench test system to verify conceptual functional operation of optical modules in accordance with the preferred embodiment. FIG. 3 shows detection limit for 10 and 20 second exposures. Measured and averaged backgrounds 30517DLU for 20 sec and 19182DLU for 10 sec were subtracted from the averaged total fluorescence signals represented in Table B for the bioarray map of Table A.

Oligonucleotide was synthesized on a 394 DNA/RNA synthesizer (Applied Biosystems Inc., Foster City, Calif., US) by standard phosphoramidite chemistry. Oligonucleotide contains 3'-terminal amino group introduced by use of 3'-Amino-Modifier C7 CPG 500 (Glen Research Corporation, Sterling, Va., US). Solutions obtained after deprotection procedure was purified by reverse phase HPLC (Dinamax; Rainin Instrument Co., Inc.), evaporated to dryness (CentiVap concentrator, Labconco, Kansas City, Mo., US) and redissolved in Milli-Q water to final concentration of 2 mM. Oligonucleotide was labeled by Texas Red sulfonyl chloride (Invitrogen Corporation, Carlsbad. Calif., US) according to manufacturer protocol and purified by reverse phase HPLC.

Initial solution of TR-TTTTTTTT-NH2 in the D water was prepared in accordance with Table B below. A test bioarray 102 was manufactured in accordance of the method disclosed in the above-described U.S. Pat. No. 6,458,584 as indicated in the Bioarray map of Table A below and then was measured.

TABLE A

Bioarray map

| | | | | |
|---|---|---|---|---|
| 20 | 12 | 12 | 12 | 20 |
| 13 | 13 | 12 | 12 | 12 |
| 13 | 13 | 13 | 13 | 13 |
| 14 | 14 | 14 | 13 | 13 |
| 14 | 14 | 14 | 14 | 14 |
| 15 | 15 | 15 | 15 | 14 |
| 15 | 15 | 15 | 15 | 15 |
| 16 | 16 | 16 | 16 | 16 |
| 16 | 16 | 16 | 16 | 17 |
| 17 | 17 | 17 | 17 | 17 |
| 17 | 17 | 17 | 18 | 18 |
| 18 | 18 | 18 | 18 | 18 |
| 18 | 18 | 19 | 19 | 19 |
| 19 | 19 | 19 | 19 | 19 |
| 19 | 20 | 20 | 20 | 20 |
| 20 | 20 | 20 | 20 | 20 |

TABLE B

| | | Calculated detection limit | | | | | |
|---|---|---|---|---|---|---|---|
| | Probe | Exposure time 20 sec | | | Exposure time 10 sec | | |
| Probe# | concentration, C fmol/ul | Average [DLU] | STDEV [DLU] | CONFIDENCE [DLU] | Average [DLU] | STDEV [DLU] | CONFIDENCE [DLU] |
| 12 | 20 | 15554 | 1668 | 1090 | 10228 | 837 | 547 |
| 13 | 39 | 19266 | 2005 | 1310 | 12646 | 1046 | 683 |
| 14 | 78 | 22990 | 1790 | 1169 | 14944 | 1110 | 725 |
| 15 | 156 | 26764 | 1951 | 1275 | 16412 | 888 | 580 |
| 16 | 313 | 30208 | 2666 | 1742 | 18995 | 1281 | 837 |
| 17 | 625 | 35748 | 2971 | 1941 | 22691 | 2127 | 1390 |
| 18 | 1250 | 50422 | 5896 | 3852 | 30743 | 3053 | 1995 |
| 19 | 2500 | 65491 | 3588 | 2344 | 39327 | 1899 | 1241 |
| 20 | 5000 | 89722 | 5864 | 3466 | 52710 | 4644 | 2744 |

TABLE 1

Calculated data of test bioarray measured by bioarray reader (ANL MCR). Lens focused on bioarray element.

|  | Averaged total signals per bioarray element [DLU] | | Averaged total signals per pixel [DLU] | |
| --- | --- | --- | --- | --- |
|  | Element bioarray | Background | Average inner | Average outer |
| Average | 3121 | 751 | 16 | 6 |
| STDEV | 455 | 78 | 2 | 1 |
| Confidence | 117 | 20 | 0.6 | 0.3 |
| Ratio S/B | 4.2 | | 2.5 | |

TABLE 2

Calculated data of test bioarray measured by bioarray reader (ANL MCR). Lens was defocused. Focus plane was above of bioarray element on the distance of 1.1 mm

|  | Averaged total signals per bioarray element [DLU] | | Averaged total signals per pixel [DLU] | |
| --- | --- | --- | --- | --- |
|  | Value | Background | Value | Background |
| Average | 2567 | 587 | 13 | 4 |
| STDEV | 536 | 82 | 3 | 1 |
| Confidence | 138 | 21 | 0.7 | 0.2 |
| Ratio S/B | 4.4 | | 3.3 | |

Bioarray containing fluorescent die in elements 4 (100 replicas), with element size 100×100 microns and spaced for 300 microns center to center on the glass support was measured by ANL Bioarray reader (model 04). Bioarray was placed face up with elements 104 on thermo-controlled table 10 therewith top surface of elements 104 were in the focus of the Lens and measured. Then bioarray was flip vertically and measurements made with no refocusing. Comparison of calculated data represented in Table 1 and Table 2 shows that elements 4 defocusing does not change quality of measurements as far as elements projection on the CCD chip are not overlapped, that simplified optical module assembly and allows the use simple inexpensive optics.

While the present invention has been described with reference to the details of the embodiments of the invention shown in the drawing, these details are not intended to limit the scope of the invention as claimed in the appended claims.

What is claimed is:

1. A modular, micro-scale, optical array and biodetection device for quantifying fluorescence intensities of a plurality of substantially separated, and dimensionally uniform elements of a bioarray, said bioarray elements located at known positions on a plain support comprising:
   a light guide directing bioarray illumination light from a respective light source to opposing sides of the plain support;
   an optical module collecting light individually from the bioarray elements; said optical module including an optical member, a filter, and a sensor;
   said optical member collects and transfers emitted light from the bioarray elements via the filter to the sensor; said optical member including a micro-lens array and a fiber optic faceplate;
   said micro-lens array focusing emitted light from the bioarray elements, said micro-lens array having consistent scale and dimensionality with the bioarray elements;
   said filter transfers light from the elements having a predefined wavelength spectrum and blocks light outside the predefined wavelength spectrum; and said sensor receives transferred light from the elements and produces a signal corresponding to respective elements of the bioarray.

2. A modular, micro-scale, optical array and biodetection device as recited in claim 1 wherein said sensor is a charge-coupled-device (CCD) chip.

3. A modular, micro-scale, optical array and biodetection device as recited in claim 1 wherein said fiber optic faceplate has consistent scale and dimensionality with the bioarray elements, said fiber optic faceplate transferring emitted light from the bioarray elements.

4. A modular, micro-scale, optical array and biodetection device as recited in claim 1 wherein said filter is located below said optical member proximate to said bioarray.

5. A modular, micro-scale, optical array and biodetection device as recited in claim 1 wherein said filter is located above said optical member proximate to said sensor.

6. A modular, micro-scale, optical array and biodetection device as recited in claim 1 wherein said optical member proximate to said bioarray.

7. A modular, micro-scale, optical array and biodetection device as recited in claim 1 wherein said fiber optic faceplate is located proximate to said bioarray.

8. A modular, micro-scale, optical array and biodetection device as recited in claim 1 wherein said filter is located between said micro- lens array and said fiber optic faceplate.

9. A modular, micro-scale, optical array and biodetection device as recited in claim 1 wherein said filter is located proximate to said sensor above said micro-lens array and said fiber optic faceplate.

10. A modular, micro-scale, optical array and biodetection device as recited in claim 1 wherein said sensor includes a charge coupled device (CCD) chip.

11. A modular, micro-scale, optical array and biodetection device as recited in claim 1 includes a reaction chamber, said reaction chamber containing said bioarray elements.

12. A modular, micro-scale, optical array and biodetection device as recited in claim 11 includes a temperature control coupled to said reaction chamber.

13. A modular, micro-scale, optical array and biodetection device as recited in claim 12 wherein said temperature control coupled said reaction chamber for controlling temperature in a range between from +4° C. and +95° C.

14. A modular, micro-scale, optical array and biodetection device as recited in claim 11 wherein said reaction chamber includes at least two ports.

* * * * *